United States Patent [19]

Frisbie

[11] Patent Number: 5,069,619
[45] Date of Patent: Dec. 3, 1991

[54] DENTAL IMPRESSION TRAY WITH LEVEL INDICATOR

[76] Inventor: Michael G. Frisbie, 1992 Millville Ct., Thousand Oaks, Calif. 91360

[21] Appl. No.: 425,125

[22] Filed: Oct. 23, 1989

[51] Int. Cl.⁵ .......................... A61C 19/04; A61C 9/00
[52] U.S. Cl. ......................................... 433/72; 433/68; 433/71; 433/214
[58] Field of Search ....................... 433/68, 69, 70, 71, 433/72, 75, 214

[56] References Cited

U.S. PATENT DOCUMENTS

| | | | |
|---|---|---|---|
| 1,070,123 | 8/1913 | Evans | 433/69 |
| 1,505,792 | 8/1924 | Ludlum | 433/214 X |
| 2,548,817 | 4/1951 | Raiche | 433/72 X |
| 2,758,375 | 8/1956 | Badovinac et al. | 433/68 |
| 4,762,491 | 8/1988 | Bolton | 433/72 |

FOREIGN PATENT DOCUMENTS

| | | | |
|---|---|---|---|
| 2539979 | 8/1984 | France | 433/72 |
| 2539981 | 8/1984 | France | 433/72 |

Primary Examiner—Robert P. Swiatek
Assistant Examiner—Nicholas D. Lucchesi
Attorney, Agent, or Firm—Kelly Bauersfeld & Lowry

[57] ABSTRACT

A dental impression tray or bite registration tray or the like is provided with a level indicator to indicate patient bite angle. When the impression tray or the like is placed into the mouth of a patient, the level indicator provides an accurate indication of patient bite angle, particularly with respect to deviations from a horizontal plane. This bite angle information can be used subsequently in dental laboratory procedures to accommodate the specific bite angle in the formation of a dental prosthesis or the like, thereby achieving a more accurate prosthesis fit.

19 Claims, 3 Drawing Sheets 5,069,619

DENTAL IMPRESSION TRAY WITH LEVEL INDICATOR

BACKGROUND OF THE INVENTION

This invention relates generally to improvements in dental devices and procedures used in the formation of custom fitted dental prostheses, such as crowns, bridges, veneers, and the like. More particularly, this invention relates to improvements in dental impression or bite registration trays which incorporate relatively simple and easily manipulated means for indicating patient bite angle, thereby permitting formation of the prosthesis in accordance with patient bite angle.

Dental prostheses such as crowns, bridges, veneers, etc. and related dental procedures are well known in the art for restoring damaged or missing teeth within the mouth of a patient. In general terms, the area to be restored is initially prepared by the dentist, such as by reducing a damaged tooth by drilling and shaping procedures to form a suitable base adapted to receive and support a prosthetic crown. The prepared area including adjacent and opposing tooth and gum structures is then replicated by means of a dental impression defined typically by a curable vinyl elastomer or the like carried on a suitably shaped impression tray which is placed into the patient's mouth for the duration of a short cure cycle. The dental impression is then used to form the appropriate mold or molds from which the desired dental prosthesis is formed, normally from a castable gold alloy or the like. Other types of dental prostheses may require an imprint of the patient's bite registration in lieu of a dental impression.

The dental impression or bite imprint is commonly fitted into a dental articulator in the course of producing the requisite mold or molds for the final prosthesis. However, in accordance with standard dental laboratory procedures, the dental articulator is oriented horizontally to correspondingly reproduce a horizontal patient bite line or angle. Unfortunately, the actual bite angle in many patients deviates from a horizontal plane. As a result, the prosthesis is shaped for precision custom fit according to a horizontal patient bite line which does not in fact exist. When the dentist attempts to place the prosthesis into the patient's mouth, an improper or unsatisfactory fit is recognized. Since most bite angle deviations are relatively small, the dentist normally tries to remedy the prosthesis misfit by trial and error grinding of the prosthesis. This approach can be extremely costly to the dentist by substantially increasing the time needed for proper prosthesis fit and placement. Moreover, and more importantly, trial and error attempts to reshape the prosthesis often result in a poor fit and resultant poor service life and patient dissatisfaction.

In the past, dental appliances have been proposed particularly in the field of orthodontics for use in measuring the patient bite line or angle. However, such appliances have been relatively costly and difficult to use, and further have not provided a bite angle indication which can be satisfactorily communicated to and reproduced at a dental laboratory located typically at a different facility. Accordingly, in spite of the aforementioned problems attributable to bite angle variations, the general dental practice has been to ignore the problem or otherwise accommodate bite angle deviations by estimation and/or trial and error procedures.

There exists, therefore, a significant need for further improvements in dental appliances and methods, particularly with respect to the provision of relatively simple yet accurate means for indicating patient bite angle. The present invention fulfills these needs and provides further related advantages.

SUMMARY OF THE INVENTION

In accordance with the invention, a dental impression or bite registration tray includes a level indicator for providing an accurate indication of patient bite angle. The bite angle indication permits reproduction of patient bite angle in a restorative dental prosthesis, thereby providing improved prosthesis fit.

In one preferred form of the invention, a dental impression or bite registration tray has a level indicator mounted thereon. A preferred level indicator comprises a conventional bubble level carried by a support frame mounted movably upon a handle member which protrudes from the impression tray. When the impression tray is inserted into the mouth of a patient, the level indicator is adjusted to and locked in a substantially horizontal orientation, thereby setting the level indicator angularly with respect to the tray when the patient has a non-horizontal bite line. In this orientation, the impression tray and level indicator can be mounted as a unit upon a dental articulator with the level indicator in a horizontal orientation, thereby orienting the tray at a bite angle corresponding with the actual bite angle of the patient.

In an alternative form of the invention, a removable level indicator is adapted for removable mounting onto the protruding handle member of an impression tray or the like, and includes means for registering the actual bite angle orientation of the tray when placed into the mouth of a patient. The registered bite angle is recorded, preferably on a writable surface defined on the tray, after which the level indicator is removable for subsequent re-use. The impression tray can be reassembled with another level indicator and the resultant combined unit mounted onto a dental articulator at the registered bite angle.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
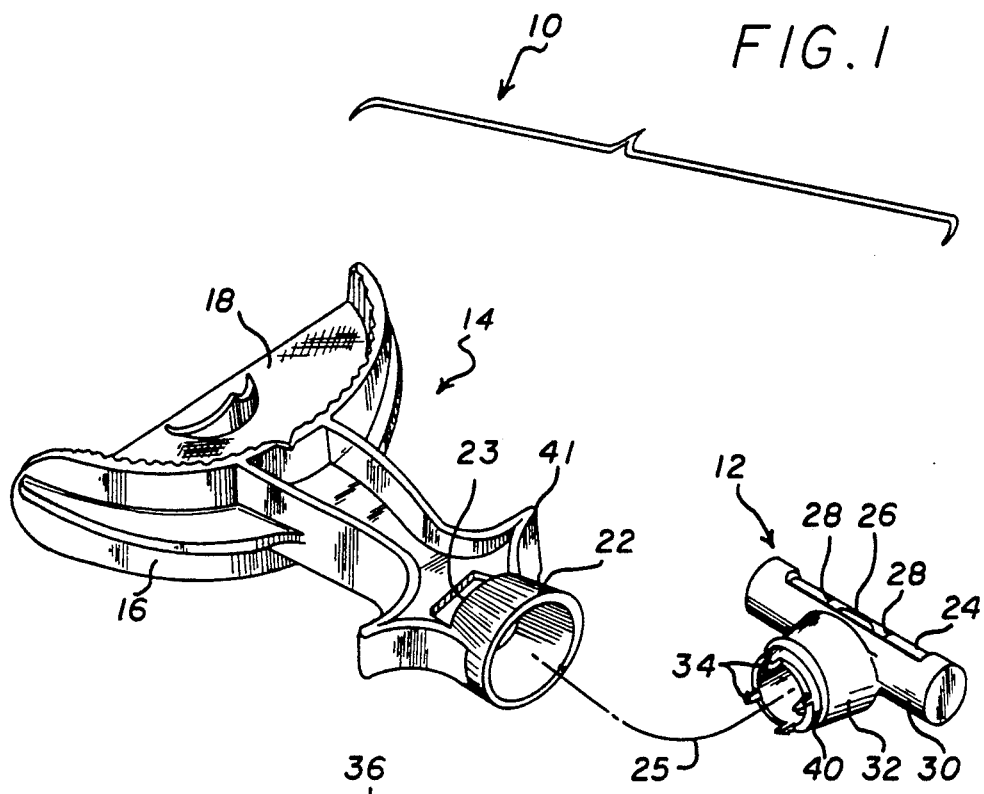
FIG. 1 is an exploded perspective view illustrating a dental impression tray with level indicator, in accordance with the novel features of the invention.

As shown in the exemplary drawings, an improved dental impression or bite registration tray referred to generally in FIG. 1 by the reference numeral 10 is adapted for assembly with a level indicator 12 for use in providing an accurate indication of patient bite angle. This indication of actual patient bite angle is conveniently communicated to a dental laboratory or the like such that the bite angle can be accurately replicated in a dental prosthesis, such as a crown, bridge, veneer, etc., thereby insuring a substantially optimized custom prosthesis fit and resultant prolonged service life.

The combined dental impression tray and level indicator of the present invention provides a simple, easy-to-use and accurate device to permit patient bite angle to be taken into account in the formation of custom fitted dental prostheses. In this regard, many dental patients exhibit a bite line or angle which deviates from a horizontal plane by perhaps one or two degrees, with bite line deviations of as much as five to ten degrees occasionally occurring. In standard restorative dentistry, the dentist normally uses a dental impression tray or similar device to form a resilient model of a selected tooth and gum area prepared for a restorative prosthesis, or otherwise to produce a bite imprint, for subsequent use at a dental laboratory to form a custom fitted prosthesis. However, such impression or bite registration imprint does not reflect true patient bite angle, and the laboratory normally proceeds to form the prosthesis based upon an assumed horizontal bite line. When the dentist then attempts to install the prosthesis, an improper fit frequently results due to the failure to accommodate bite angle. The present invention provides a simplified device and method for accommodating actual bite angle when the prosthesis is formed, to correspondingly provide improved prosthesis fit with reduced installation time required by the dentist.

FIG. 1 illustrates the dental impression tray 10 having a mouthpiece 14 of generally known design for use in replicating portions of tooth and/or gum structures within the mouth of a patient. The exemplary mouthpiece 14 includes a generally upright forward wall 16 of molded plastic or the like formed with an arcuate curvature approximating the shape of the tooth line. This wall 16 supports a thin paper-based membrane 18 which is oriented generally horizontally with the arcuate wall 16 extending upwardly and downwardly therefrom. In use, the mouthpiece 14 is placed into the patient's mouth with the membrane 18 disposed between the upper and lower rows of teeth, and with the arcuate wall 16 in close proximity with the front of the patient's teeth. In accordance with known dental techniques, the membrane 18 may support an impression material (not shown) such as a curable vinyl elastomer or the like. When an impression material is used, the tray is placed into the patient's mouth with the curable material pressed about a selected tooth and gum region for the duration of a cure cycle to produce a resilient mold. Alternately, as is also known in the art, the tray may be used to produce a bite registration imprint on the membrane 18. Accordingly, it will be understood that the illustrative impression tray 10 represents a dental device used to replicate or otherwise obtain information regarding the geometry of selected portions of a patient's mouth.

A handle member 20 of molded plastic or the like is formed integrally with the curved wall 16 and protrudes forwardly therefrom to provide a convenient structure for handling and manipulating the mouthpiece 14. As shown best in FIGS. 1, 5 and 6, the forwardmost end of the handle member 20 includes a generally cylindrical support sleeve 22 formed preferably with a slight conical taper expanding in a forward direction away from the mouthpiece. This support sleeve 22 is sized and shaped for receiving and supporting the level indicator 12. In this regard, the illustrative preferred form of the invention provides the level indicator in the form of a conventional bubble level of the type having a vial 24 containing a fluid is sufficient quantity to define a bubble 26 which, when the bubble is located between indicator marks 28 on the vial, indicates a level condition. The vial 24 is carried on a support frame 30 of molded plastic or the like to include a guide cylinder 32 adapted for relatively close mating fit reception into the support sleeve 22 on the handle member, as will be described. Locking fingers 34 on the leading end of the cylinder 32 are provided for snap-fit engagement with an inboard margin 23 of the support sleeve 22 to hold the support frame 30 on the handle member while permitting rotation of the support frame about a central axis 25 of the support sleeve 22. As shown in FIG. 1, this sleeve axis 25 corresponds with a median axis of the impression tray 10.

Figure 2:
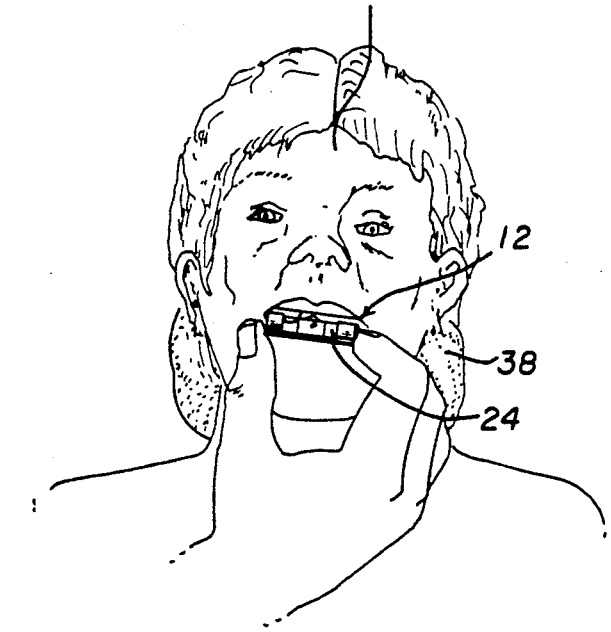
FIG. 2 is a pictorial illustration showing initial placement of the impression tray into the mouth of a patient.
Figure 3:
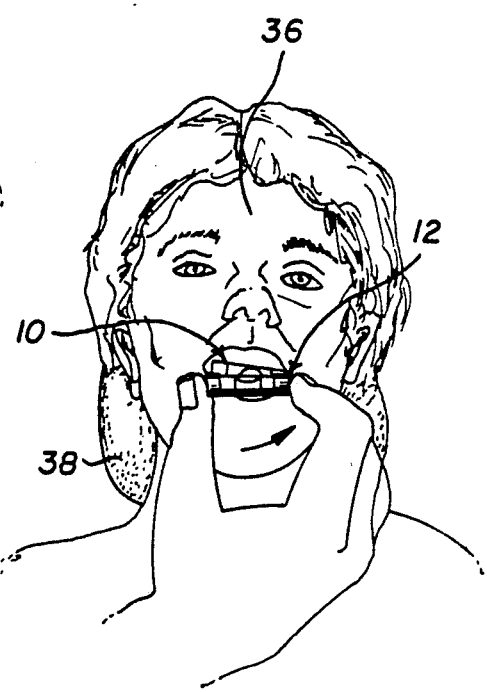
FIG. 3 is a pictorial illustration similar to FIG. 2, but depicting adjustment of the level indicator to provide an indication of patient bite angle.
Figure 5:
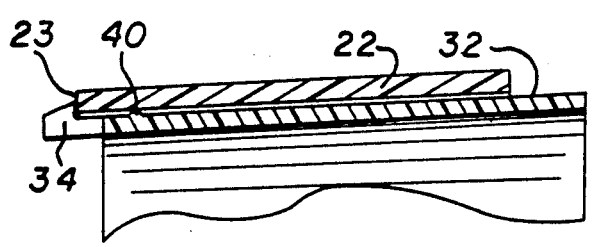
FIG. 5 is a further enlarged, fragmented sectional view taken generally on the line 5—5 of FIG. 4.
Figure 6:
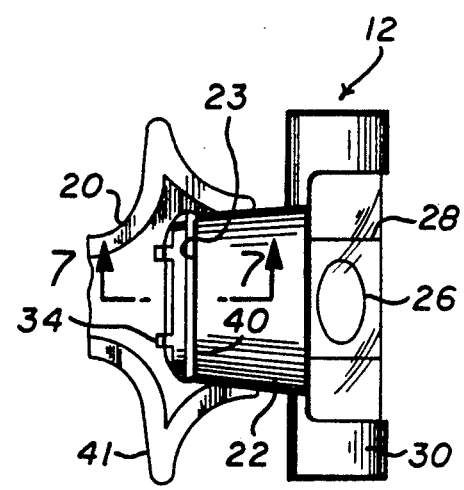
FIG. 6 is an enlarged and fragmented top plan view similar to FIG. 4, but illustrating the level indicator in locked relation with the impression tray.
Figure 7:
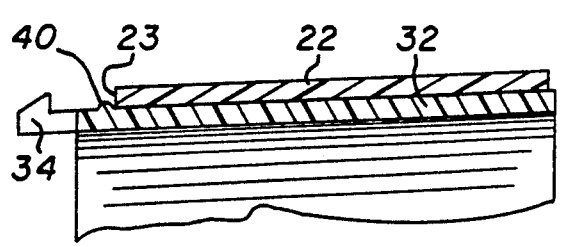
FIG. 7 is an enlarged fragmented sectional view taken generally on the line 7—7 of FIG. 6.

In use, as viewed in FIG. 2, the impression tray in placed into the mouth of a patient 36 in the course of making the desired dental impression, bite registration imprint, etc. The tray 10 is placed between the upper and lower teeth, and the patient is normally asked to bite down appropriately upon the membrane 18. This procedure orients the impression tray 10 in accordance with the specific patient bite angle. Throughout this process, the patient 36 is normally seated comfortably in a partially reclined position with the head rested firmly upon the headrest 38 of a dental chair. The dentist may additionally position the patient's head in a normal upright position. If the patient's bite line or angle deviates from a horizontal plane, the level indicator 12 will provide an off-level or non-horizontal reading (FIG. 2) when the vial 24 is parallel with the membrane 18. In this event, the dentist rotates the level indicator 12 within the support sleeve 22 to provide a horizontal reading, as viewed in FIG. 3, thereby re-orienting the level indicator to an angular setting relative to the membrane 18. Such rotation of the level indicator 12 may be performed relatively easily due to a minor clearance tolerance between the support sleeve 22 and the guide cylinder 32, as shown in FIG. 5. When the level reading is obtained, the dentist locks the level indicator 12 against further rotational adjustment by advancing or pressing the cylinder 32 on the support frame 30 further into the support sleeve 22 of the handle member. This motion displaces a circumferential lock ring 40 on the guide cylinder 32 through the support sleeve 22 for snap-fit engagement of the lock ring 40 against the inboard edge or margin 23 of the sleeve 22 (FIGS. 6 and 7). In this position, the guide cylinder 32 is advanced into a tight friction fit within the support sleeve to preclude further rotational adjustment of the level indicator. Laterally outwardly projecting wings 41 on the handle member 20 facilitate this locking action as a one-handed procedure.

Figure 8:
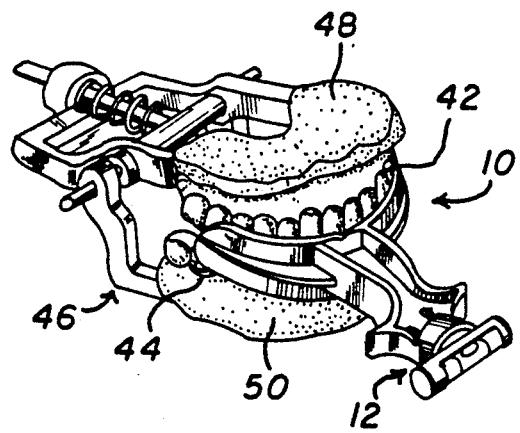
FIG. 8 is a perspective view showing use of the impression tray and level indicator in combination with a dental articulator, for use in reproducing patient bite angle in the course of forming a dental prosthesis.
Figure 4:
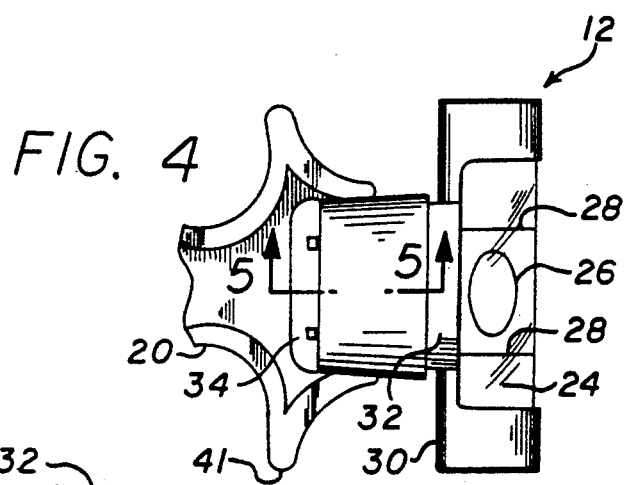
FIG. 4 is an enlarged and fragmented top plan view of a portion of the level indicator and impression tray of FIG. 1.

The combined tray and level indicator unit can then be used to produce the desired dental prosthesis with accurate replication of patient bite angle. More particularly, as viewed by way of example in FIG. 8, dental impressions made with the use of the tray 10 can be utilized to produce conventional stone models 42 and 44 which replicate all or portions of the patient's tooth and gum structures. These models are mounted into a standard dental articulator 46 having upper and lower jaw portions for connection to the models by means of upper and lower plaster masses 48 and 50, respectively. The articulator 46 is placed upon a substantially horizontal surface, and the stone models 42 and 44 are mounted onto the plaster masses before the plaster sets. The impression tray 10 with level indicator 12 attached is placed between the tooth models, and manually oriented within the still deformable plaster until the level indicator 12 provides a level reading. When the level reading is obtained, the impression tray is oriented at the actual bite angle of the patient. The plaster is then allowed to set, whereupon the tray and level indicator may be removed and discarded. The dental technician can then proceed with prosthesis formation using the mounted models, with the finished prosthesis accounting for patient bite angle.

Figure 9:
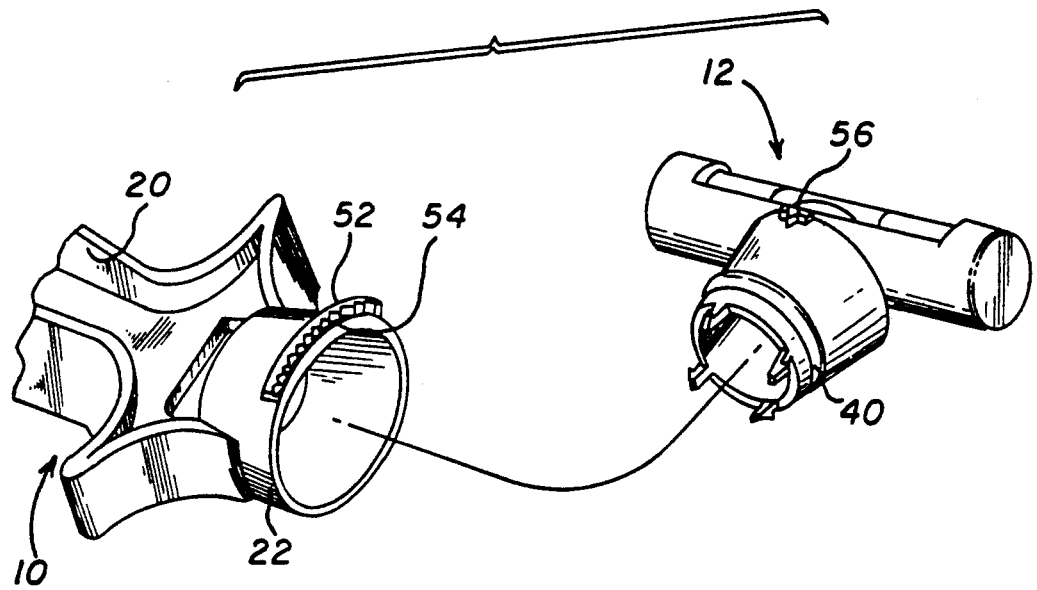
FIG. 9 is an enlarged and exploded fragmented view similar to a portion of FIG. 1, but illustrating one alternative preferred form of the invention.

FIG. 9 illustrates an alternative preferred form of the invention. In this version, the impression tray 10 and level indicator 12 correspond with those shown and described in FIGS. 1–8, except that additional locking means are provided for positively locking the level indicator 12 against rotation relative to the handle member 20. More particularly, the exterior of the handle member support sleeve 22 includes a raised lock bar 52 defining relatively fine radially oriented serrations 54 presented toward the level indicator. A small and relatively sharp lock tooth 56 is formed on the support frame 30 for engaging the serrations 54 when the lock ring 40 is pressed to the locked position (FIGS. 6 and 7), thereby positively locking the level indicator relative to the impression tray. The width of the lock bar 52 is chosen to accommodate substantial rotation of the level indicator through a range of about ten to twenty degrees in either direction from a median point in parallel relation with the membrane 18. However, it will be understood that a rotational range of about two degrees to five degrees in either direction will accommodate the necessary adjustment for most patients.

Figure 10:
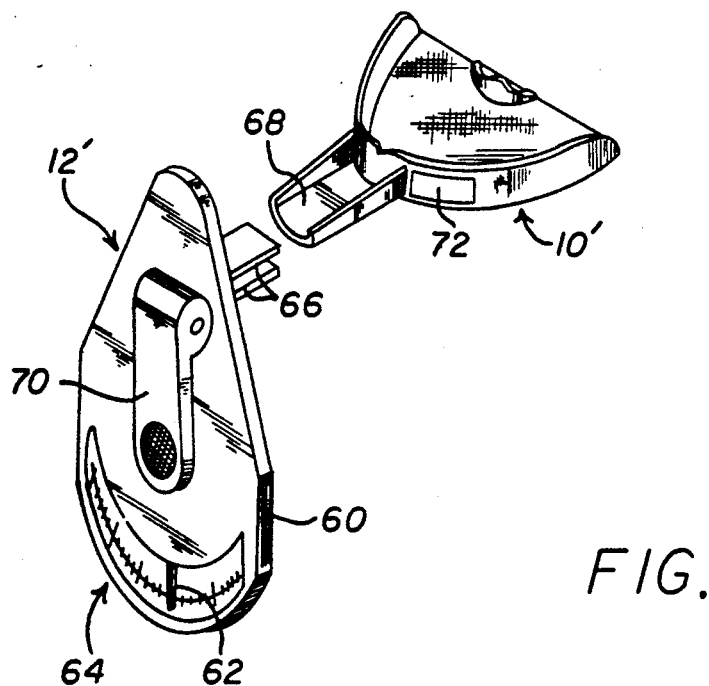
FIG. 10 is an exploded perspective view depicting another alternative preferred form of the invention.

FIG. 10 illustrates an alternative level indicator 12' of a type adapted for removal from a modified impression tray 10', thereby permitting re-use of the level indicator. In this embodiment, the level indicator 12' includes an indicator unit 60 of the type having a pendulum style pointer 62 or other suitable indicator adapted to reference off-level orientation in either direction by association with a reference scale 64. Mounting feet 66 on the unit 60 are designed to slidingly interlock with a protruding tongue 68 on the tray 10', through pivoted operation of a cammed lock lever 70 or any other suitable releasable locking means. The unit 60 is mounted onto the tray 10' in the course of making a dental impression or the like, such that an off-level patient bite angle will be indicated by the pointer 62. The dentist can record the magnitude and direction of the patient bite angle preferably directly onto a writing surface 72 located on the exterior of the tray 10'. A dental technician can subsequently use the tray in association with a similar removable level indicator unit 60 at the dental laboratory to replicate the patient bite angle, as previously described with respect to FIG. 8.

A variety of further modifications and improvements to the present invention will become apparent to those persons skilled in the art. Accordingly, no limitation on the invention is intended by way of the foregoing description and drawings, except as set forth in the appended claims.

What is claimed is:

1. In combination:
   bite registration means adapted to be inserted into the mouth of a patient between the upper and lower patient teeth to extend when contacted by the upper and lower patient teeth generally along an approximate horizontal plane extending transversely through the patient's mouth and along the patient's bite line; and
   level indicator means mounted on said bite registration means at a position directly in front of the patient's mouth when said bite registration means is contacted by the upper and lower patient teeth to extend generally along said proximate horizontal plane for referencing deviations of said approximate horizontal plane from a true horizontal orientation and thereby reference the angle of the patient's bite line.

2. The combination of claim 1 wherein said bite registration means comprises an impression tray.

3. The combination of claim 1 wherein said bite registration means comprises a bite registration tray.

4. The combination of claim 1 wherein said level indictor means is movably mounted on said bite registration means to permit adjustment of said level indicator means to a substantially true horizontal orientation.

5. The combination of claim 4 further including means for locking said level indicator means against further adjustment with respect to said bite registration means.

6. The combination of claim 1 wherein said level indicator means is removably mounted on said bite registration means.

7. The combination of claim 6 wherein said level indicator means includes reference scale means for indicating the magnitude and direction of off-level position of said bite registration means, said bite registration means including a writable surface to permit off-level magnitude and direction information to be written thereon.

8. The combination of claim 1 wherein said level indicator means comprises a bubble level.

9. In combination:
   a dental mouthpiece adapted to be inserted into the mouth of a patient between the upper and lower patient teeth to extend when contacted by the upper and lower patient teeth generally along an approximate horizontal plane extending transversely through the patient's mouth and along the patient's bite line;
   a handle member protruding from said mouthpiece to a position outside and in front of the patient's mouth when the mouthpiece is inserted into the patient's mouth; and a level indicator means mounted on said handle member directly in front of the patients mouth for referencing deviations of said approximate horizontal plane from a true horizontal orientation and thereby reference the angle of the patient's bite line when said mouthpiece extends along the patient's bite line.

10. The combination of claim 9 wherein said level indicator is rotatably mounted onto said handle member, said level indicator being adjustable rotatably to a substantially level position when said mouthpiece extends along the patient's bite line to reference the patient's bite angle.

11. The combination of claim 10 further including means for locking said level indicator against further rotation relative to said handle member.

12. The combination of claim 9 wherein said level indicator comprises a bubble level.

13. The combination of claim 9 wherein said level indicator is removably mounted on said handle member in a predetermined orientation, at least one of said handle member and said mouthpiece having a writable surface defined thereon.

14. In combination:
a dental mouthpiece adapted to be inserted into the mouth of a patient between the upper and lower patient teeth to extend generally along the patient's bite line;
a handle member protruding from said mouthpiece to a position outside the patient's mouth when the mouthpiece is inserted into the patient's mouth, said handle member including a generally cylindrical support sleeve having a tapered conical geometry expanding and opening in a direction away from said mouthpiece;
a level indicator mounted on said handle member for referencing the angle of the patient's bite line when said mouthpiece extends along the patient's bite line, said level indicator being rotatably mounted onto said handle member and being adjustable rotatably to a substantially level position when said mouthpiece extends along the patient's bite line to reference the patient's bite angle, said level indicator further including a guide cylinder adapted for substantially mated reception into said support sleeve whereby said guide cylinder is rotatable within said support sleeve; and
means for locking said level indicator against further rotation relative to said handle member.

15. The combination of claim 14 wherein said guide cylinder includes a plurality of snap-fit locking fingers for normally engaging an edge of said support sleeve presented toward said mouthpiece, when said guide cylinder is received into said support sleeve, said guide cylinder being rotatable within said support sleeve when said fingers engage said sleeve edge, said guide cylinder further having a raised outer lock ring thereon for press-fit advancement through said support sleeve to engage said support sleeve edge, said guide cylinder being tightly received into said support sleeve to prevent relative rotation therebetween when said lock ring engages said sleeve edge.

16. A method of indicating the bite line angle of a dental patient, said method comprising the steps of:
mounting a level indicator onto a dental mouthpiece; and
inserting the dental mouthpiece into the mouth of a patient so that said level indicator is directly in front of the patient's mouth between the upper and lower patient teeth such that the mouthpiece extends when contacted by the upper and lower patient teeth generally along an approximate horizontal plane extending transversely through the patient's mouth and along the patient's bite line and the level indicator provides an indication of any deviation between the approximate horizontal plane and a true horizontal plane thereby providing an indication of patient bite line angle.

17. The method of claim 16 further including the step of adjusting the level indicator to a level orientation while the mouthpiece extends along the approximate horizontal plane referencing the patient's bite line.

18. The method of claim 17 further including the step of locking the level indicator against further adjustment after the level orientation has been reached.

19. The method of claim 16 further including the step of reading and recording the orientation of the level indicator while the mouthpiece extends along the approximate horizontal plane referencing the patient's bite line.

* * * * *